United States Patent [19]
Fleenor

[11] Patent Number: 5,306,238
[45] Date of Patent: * Apr. 26, 1994

[54] LAPAROSCOPIC ELECTROSURGICAL PENCIL

[75] Inventor: Richard P. Fleenor, Englewood, Colo.

[73] Assignee: Beacon Laboratories, Inc., Broomfield, Colo.

[ * ] Notice: The portion of the term of this patent subsequent to Mar. 24, 2009 has been disclaimed.

[21] Appl. No.: 759,401

[22] Filed: Sep. 13, 1991

Related U.S. Application Data

[63] Continuation-in-part of Ser. No. 495,449, Mar. 16, 1990, Pat. No. 5,098,430.

[51] Int. Cl.⁵ .............................................. A61B 17/39
[52] U.S. Cl. ........................................ 606/42; 606/45; 606/49
[58] Field of Search ............... 606/41, 42, 45, 49, 606/22; 219/121.5, 121.51

[56] References Cited

U.S. PATENT DOCUMENTS

| | | | |
|---|---|---|---|
| 2,618,267 | 11/1952 | Hanriot | 128/303.14 |
| 2,708,933 | 5/1955 | August | 128/303.14 |
| 2,828,747 | 4/1958 | August | 128/303.14 |
| 3,434,476 | 3/1969 | Shaw et al. | 606/22 |
| 3,562,486 | 2/1971 | Hatch | 219/121.52 |
| 4,040,426 | 8/1977 | Morrison, Jr. | 128/303.17 |
| 4,060,088 | 11/1977 | Morrison, Jr. et al. | 219/121.51 |
| 4,562,838 | 1/1986 | Walker | 128/303.14 |
| 4,719,914 | 1/1988 | Johnson | 606/45 X |
| 4,781,175 | 11/1988 | McGreevy et al. | 128/303.17 |
| 4,901,719 | 2/1990 | Trenconsky et al. | 606/49 |
| 4,911,159 | 3/1990 | Johnson et al. | 606/45 X |
| 5,098,430 | 3/1992 | Fleenor | 606/42 X |

Primary Examiner—Lee S. Cohen
Attorney, Agent, or Firm—Sheridan Ross & McIntosh

[57] ABSTRACT

An electrosurgical apparatus (10) is disclosed wherein the electrode (12) and nozzle (14) can be maintained in a nested arrangement when the apparatus (10) is in inactive operation, such as when the electrode (12) is being positioned for surgery or when the apparatus (10) is not in use. The apparatus (10) may be employed for gas-enhanced electrosurgery with the electrode (12) and nozzle (14) in the nested arrangement, the apparatus (10) thereby functioning as a dual mode, conventional electrosurgery and gas-enhanced electrosurgery, instrument. Embodiments are disclosed which are adapted for laparoscopic applications.

24 Claims, 5 Drawing Sheets

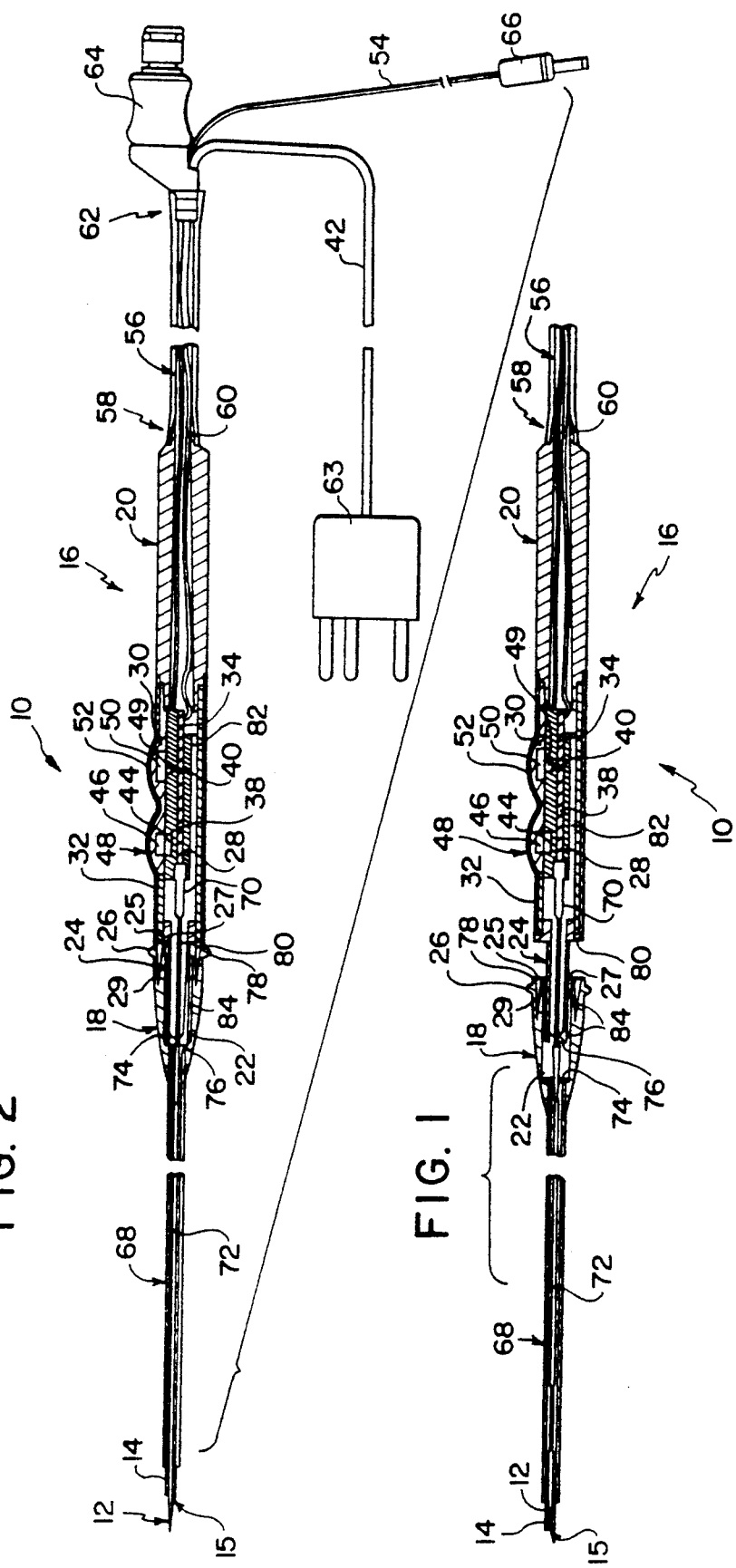

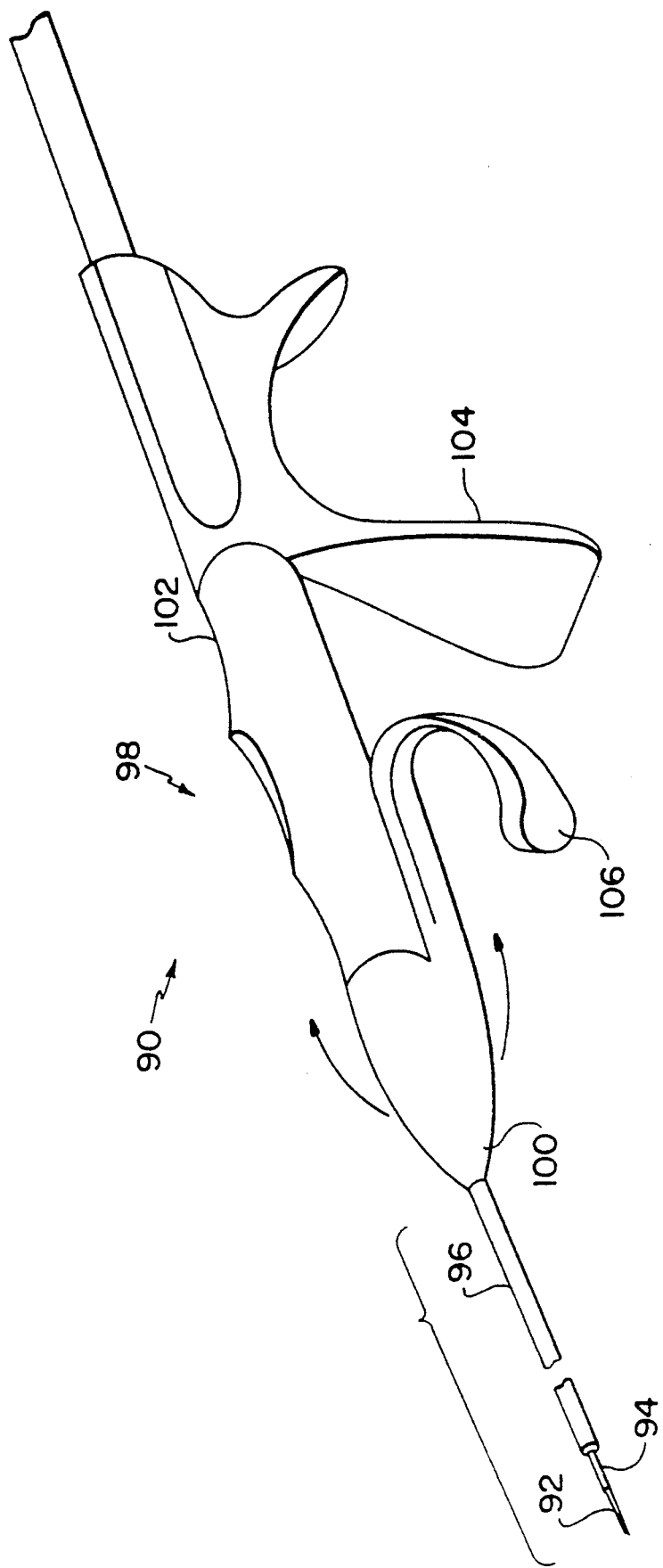

LAPAROSCOPIC ELECTROSURGICAL PENCIL

This application is a continuation-in-part application of copending U.S. patent application No. 07/495,449, now U.S. Pat. No. 5,098,430, which is incorporated herein by reference in its entirety.

1. Field of the Invention

This invention relates in general to electrosurgical instruments and, in particular, to a dual-mode, conventional electrosurgery and gas-enhanced electrosurgery, pencil which can be particularly adapted for use in laparoscopic applications.

2. Background of the Invention

Conventional electrosurgery, i.e., surgical procedures wherein a pencil including an electrode is contacted and/or positioned in close proximity to tissue, is well known. Such techniques involve the application of radio frequency (RF) electrical energy to the tissue to be treated. It is an advantage of conventional electrosurgery that the electrode can cut or coagulate depending, in part, on the characteristics of the electrical signal provided to the electrode. For example, a surgeon may change the surgical mode by changing the waveform and power of the signal.

More recently, gas-enhanced electrosurgical pencils have been utilized to achieve fulguration. In gas-enhanced electrosurgery, a gas stream is utilized to conduct electrical energy from the electrode to the tissue. It is an advantage of gas-enhanced electrosurgery that substantially uniform electrosurgical effects can be achieved. It is a further advantage of gas-enhanced electrosurgery that such effects can be achieved without the need for contact between the electrode and tissue. Such contact is undesirable because it may result in fouling of the electrode thereby affecting instrument performance and/or necessitating a time-consuming electrode cleaning procedure or replacement of the electrode.

One advantageous application of electrosurgical devices is laparoscopic surgery. In laparoscopic surgery a laparoscope is utilized to allow a surgeon to view an internal surgical area. A laparoscope may be utilized in conjunction with an electrode inserted into a patient through an access cannula to perform surgical procedures without the need for large incisions.

While the advantages and applications of electrosurgical procedures have expanded through the years, a number of challenges remain for full realization of the attendant benefits. For example, there is generally a need for electrosurgical pencils capable of functioning in both conventional electrosurgical and gas-enhanced electrosurgical modes. That is, surgeons desiring to cut tissue in a conventional mode and fulgurate in a gas-enhanced mode commonly employ two separate pencils and possibly two separate support systems. Relative to a single pencil, the utilization of two separate pencils entails additional space requirements and a greater investment in surgical equipment. In addition, the utilization of two pencils requires double handling which may lengthen surgery particularly for laparoscopic operations.

Another challenge is to increase the safety of electrosurgical apparatus by reducing the likelihood of accidental tissue puncturing, particularly when the apparatus is inserted through narrow passageways or used in areas where the surgeon's view is limited. For example, in laparoscopic procedures with preexisting pencils, puncturing may occur if the exposed electrode is inserted too far through an access cannula. Similarly, another challenge is to reduce the risk, in certain applications, of the electrode contacting tissue or fluids as the electrode is positioned for surgery, such as when the electrode is inserted through a cannula for laparoscopic applications, thereby possibly affecting instrument performance and/or necessitating cleaning or replacement of the electrode during use.

SUMMARY OF THE INVENTION

Accordingly, objectives of the present invention include the following:

The provision of an electrosurgical pencil wherein the electrode can be disposed substantially unexposed in an inactive state, i.e., when no current is being provided to the electrode, to reduce the risk of tissue puncturing or undesirable electrode/tissue or body fluid contact as the instrument is being positioned for surgery or when the instrument is otherwise not in use.

The provision of an electrosurgical pencil, including an electrode and a nozzle which are interconnected for relative movement therebetween, wherein the electrode and nozzle can be selectively maintained in a nested arrangement when the instrument is in an inactive state.

The provision of such an electrosurgical instrument including a housing having slidably interconnected nose and tail portions, wherein one of the electrode and nozzle is interconnected to the nose portion and the other is interconnected to the tail portion for relative movement therebetween.

The provision of a dual-mode electrosurgical instrument for laparoscopic applications which can be selectively employed in a first mode for conventional electrosurgical cutting/coagulation and in a second mode for gas-enhanced fulguration.

The provision of a dual-mode electrosurgical instrument wherein a surgeon has manual control over the relative positioning of a gas delivery nozzle and an electrode.

Additional objectives and corresponding advantages will be apparent to those skilled in the art.

According to an embodiment of the present invention, an electrosurgical instrument is provided. In one aspect, the instrument comprises a surgical assembly including a nozzle and an electrode having a common longitudinal axis. The assembly is arrangeable between a first arrangement and a second arrangement, wherein the electrode is more forward relative to the nozzle in the first arrangement than in the second arrangement. In addition, the assembly can be maintained in the second arrangement when the assembly is inactive, such as when the electrode is being positioned for surgery or when the instrument is not in use. A gas delivery system can be provided to deliver gas to the nozzle for gas enhanced surgery when the assembly is arranged in the second arrangement.

According to another aspect of the present invention, an electrosurgical instrument including a pencil housing is provided. The pencil housing includes a tail portion and a nose portion which are slidably interconnected for relative movement therebetween. One of the tail portion and nose portion is interconnected to an electrode and the other is connected to a nozzle. Relative movement between the tail portion and nose portion therefore results in relative movement between the electrode and nozzle, e.g., between a nested position and a position wherein the electrode is exposed. The housing further includes an internal passageway for delivery of gas for gas enhanced surgery in the nested position.

According to another aspect of the present invention, an electrosurgical apparatus is provided which is particularly adapted for use in laparoscopic applications. The apparatus comprises a cannula, a electrode and a nozzle having a common longitudinal axis wherein the nozzle is fixedly attached to the cannula, and a positioning device for moving the electrode relative to the nozzle between a first position for non gas-enhanced electrosurgery and a second position for gas-enhanced electrosurgery wherein the electrode is more forward relative to the nozzle in the first position than in the second position.

DESCRIPTION OF THE DRAWINGS

FIG. 1 is a cross-sectional side view of an embodiment of the present invention, wherein the electrode and nozzle are positioned in a nested arrangement;

FIG. 2 is a cross-sectional side view of the embodiment of FIG. 1, wherein the electrode and nozzle are positioned so that the electrode is exposed;

FIG. 5 is a perspective view of the embodiment of FIG. 4 wherein the electrode and nozzle are positioned so that the electrode is exposed;

DETAILED DESCRIPTION OF THE INVENTION

Figure 3:
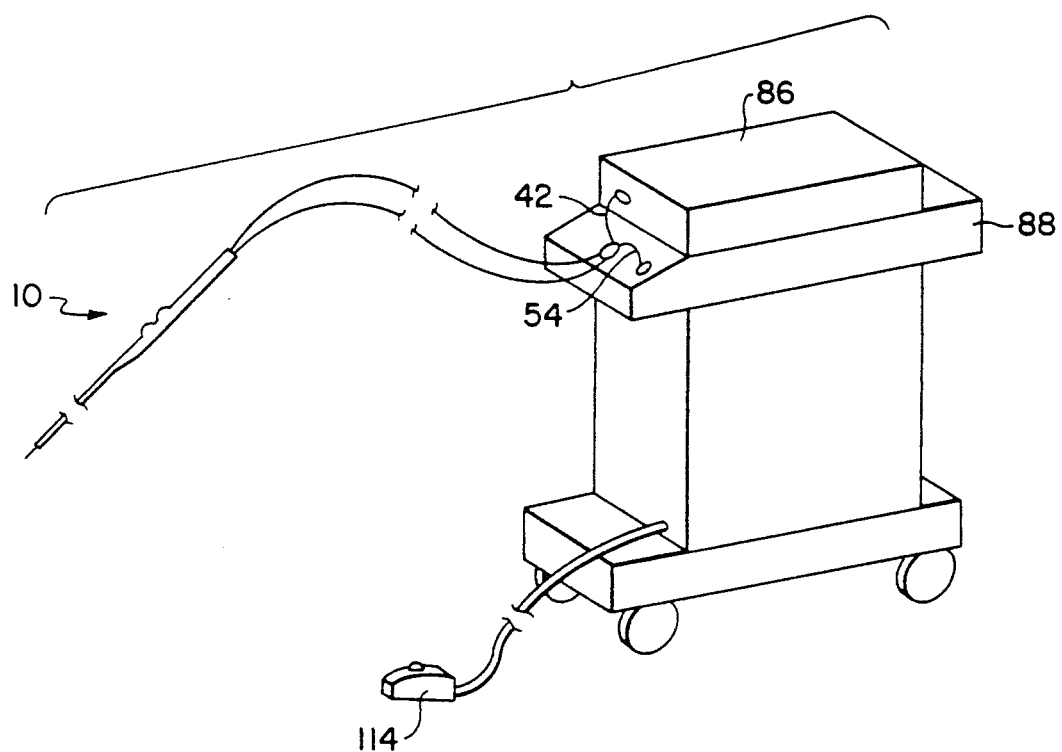
FIG. 3 shows the embodiment of FIGS. 1 and 2 interconnected for dual mode operations with an inert gas supply means and electrosurgical generator.

In FIGS. 1-3, like items are identified by like and corresponding numerals for ease of reference. Referring to FIGS. 1 and 2, an electrosurgical apparatus constructed in accordance with an embodiment of the present invention is generally identified by the reference numeral 10. The apparatus 10 comprises a surgical assembly including a conventional electrode 12, a nozzle 14 and a pencil housing 16. FIGS. 1 and 2 show the apparatus 10 wherein electrode 12 and nozzle 14 are in a nested arrangement (FIG. 1), and wherein electrode 12 is exposed (FIG. 2).

The outer configuration of the pencil housing 16 of the apparatus 10 is principally defined by cylindrical, hollow nose portion 18 and cylindrical, hollow tail portion 20. The nose and tail portions 18 and 20 may be of molded plastic construction and contoured for handling by a user. The nose portion 18 includes an interior nose cylinder 22 and the tail portion 20 includes a tail piston 24 extending therefrom for concentric, slidable adjoinment. The cylinder 22 and piston 24 are dimensioned so as to provide a friction fit therebetween, i.e., the inside diameter of the cylinder 22 and the outside diameter of the piston 24 are selected to provide resistance to sliding therebetween so that the relative positioning of the cylinder 22 and piston 24 can be adequately maintained.

Because the electrode 12 is mounted to move with the tail portion 20 and the nozzle 14 is mounted to move with the nose portion 18 as will be described below, the slidable adjoinment of nose portion 18 and tail portion 20 allows for relative movement of the electrode 12 and nozzle 14 between the nested and exposed arrangements. As shown in FIGS. 1 and 2, a radial bulge 26 is provided on the nose portion to facilitate finger control for slidably arranging the apparatus 10 between the first arrangement (FIG. 1) and the second arrangement (FIG. 2). It will be appreciated upon consideration of the description below, that the apparatus 10 can be employed in the exposed arrangement for conventional electrosurgery and in the nested position for gas enhanced electrosurgery or when the apparatus 10 is in an inactive state, such as when the electrode 12 is being positioned for surgery or when the apparatus 10 is not in use.

In the illustrated embodiment, the piston 24 is provided with circumferential sealing members 84, such as o-rings, which contribute to the friction fit between cylinder 22 and piston 24 and additionally serve, in cooperation with shoulder 25, to regulate relative movement between the cylinder 22 and piston 24. In this regard, shoulder 25 abuts against one of the sealing members 84 when the electrode 12 and nozzle 14 are in a nested position thereby providing a positive indication that the electrode 12 and nozzle 14 are nested and guarding against overextension of the nozzle 14 relative to the electrode 12. Relatedly, the shoulder 25 has a sloped surface 27, which widens radially from a forward to a back edge thereof, which cooperates with a generally "V" shaped cut-out 29 in the nose portion 18 to facilitate construction of the housing 16. As the nose portion 18 and tail portion 20 are pressed together during construction, the interaction of the sealing members 84 with the sloped surface 27 urges the shoulder 25 outwards and compresses the cut out 29 thereby allowing the shoulder 25 to pass over the sealing members 84.

A boot assembly comprising inner boot 28, intermediate boot 30 and sheath-like outer boot 32 extends through tail portion 20, and supports, orients, insulates and protects components for selective control of first conventional and second, gas-enhanced mode operations of the apparatus 10. By way of example, the interior of tail portion 20 and exterior of inner boot 28 can be matingly contoured and/or otherwise adapted for interconnection (not shown). Inner boot 28 and intermediate boot 30 can be fabricated from a resilient elastomer or polyurethane. The outer boot 32 can also be fabricated from such materials, wherein the outer boot 32 will stretch upon assembly to retainingly engage nose portion 18, intermediate boot 30 and tail portion 20, and will enhance the grip and control of apparatus 10 by a user.

Inner boot 28 protectively supports an electric circuit board 34 and electrically interconnected socket 36, and socket 36, in turn, supports and electrically interconnects with electrode 12. As shown in FIGS. 1 and 2, circuit board 34 is provided with first and second pressure snap dome switches 38 and 40, and is electrically interconnected to a three-conductor RF signal supply wire 42. Correspondingly, inner boot 28 and intermediate boot 30 support a first button 44 and button spacer 46 in an opposing relationship to the first snap dome switch 38, such that upon application of a predetermined pressure by a user to a complimentary first bulge region 48 of outer and intermediate boots 32 and 30, the first snap dome switch 38 will be closed to initiate the provision of an appropriate RF signal to the electrode 12 for conventional, first-mode tissue cutting procedures.

Similarly, inner boot 28 and intermediate boot 30 support a second button 49 and pressure switch 50, respectively, in an opposing relationship to the second snap dome switch 40, such that upon application of a predetermined pressure by a user to a complimentary second bulge region 52 of outer and inner boots 32 and 30, second snap dome switch 40 will be closed to initiate the provision of an appropriate RF signal to electrode 12 for first or second mode coagulation procedures. Pressure switch 50 is interconnected to a two-conductor gas supply signal wire 54, such that, upon the application of a predetermined pressure by a user to the second bulge region 52, delivery of an inert gas to pencil 10 will be initiated for second mode gas-enhanced fulguration procedures. It should be appreciated that, in order to yield selective control over convenient first and second mode coagulation operations of the preferred embodiment, the amount of applied pressure necessary to initiate the provision of an RF signal for coagulation should be less than the amount of applied pressure necessary to initiate inert gas flow. Relatedly, in the preferred embodiment, the first bulge region 48 and second bulge region 52 of the outer boot 32 can be color coded consistent with existing electrosurgical generator power indicators (e.g. yellow and blue, respectively), to visually assist a user in proper and efficient employment of the apparatus 10.

A gas supply hose 56 is connected at one end 58 to a nipple 60 of tail portion 20. The other end 62 of gas delivery hose 56 is connected to junction member 64, designed to interface with an inert gas supply means 88, as will be further discussed. The RF signal supply wire 42 and gas control signal wire 54 extend through the tail portion 20, gas supply hose 56, and exit from junction member 64. The RF signal supply wire 42 terminates in a standard plug 63 for interconnection with a standard electrosurgical generator 86. Similarly, gas supply signal wire 54 terminates in a two conductor plug 66 for interconnection with the inert gas supply means 76.

Although the apparatus 10 is advantageously employed and will be further described in connection with laparoscopic embodiments and applications, it will be appreciated by those skilled in the art that many of the features of the apparatus will be useful in non-laparoscopic applications.

In the illustrated embodiment, both the nozzle 14 and the nose portion 18 are fixedly interconnected, such as through adhesive or heat bonding, to cannula 68 which has an outside diameter less than the inside diameter of an access cannula. Similarly, an electrode assembly comprising tail portion electrode 70 and conductive electrode tube 72 fixedly interconnects electrode 12 to tail portion 24. Electrode 12 is slidably positioned within nozzle 14 and cannula 68 so that the apparatus 10 can be conveniently arranged between the conventional first mode arrangement of FIG. 1 and the gas-enhanced second mode arrangement of FIG. 2 by gripping bulge 26 and sliding tail piston 24 relative to nose cylinder 22. Nozzle 14, which may include a ceramic tip 15 suitable to withstand the heat generated by the apparatus 10 at the surgical site, extends beyond the end of cannula 68.

A spring or other resilient member (not shown) may be operatively disposed between the nose portion 18 and tail portion 20 to further maintain apparatus 10 in the arrangement of FIG. 1 during gas-enhanced operation or when the apparatus 10 is inactive, e.g., when the electrode 12 is being positioned for surgery. For example, a spring may be provided between cylinder wall 74 and piston wall 76 or between nose portion wall 78 and tail portion wall 80 such that the spring urges electrode 12 to assume a sufficiently retracted position relative to the nozzle 14 for gas-enhanced fulguration procedures and for protection against tissue puncturing when the apparatus 10 is inactive. More particularly, apparatus 10 should preferably be designed so that electrode 12 projects forwardly no more than approximately one-quarter inch from nozzle 14 for effective second-mode gas-enhanced fulguration. More preferably, the electrode 12 and nozzle should be substantially nested for second mode operation or when the apparatus is in inactive operation. For first-mode cutting/coagulation procedures, electrode 12 should preferably project forwardly approximately one-half inch or more from nozzle 14.

As shown in FIG. 1, the tail portion 20, nose portion 18 and boot assembly (i.e., 28 and 30) are constructed and interconnected to define inner passageway(s) 82 for the delivery of inert gas from gas supply hose 56 to the nozzle 14 during gas-enhanced second mode operations. Relatedly, sealing members 84 such as 0-rings are provided between nose cylinder 22 and tail piston 24 to reduce or eliminate gas leakage during second-mode operation. It will thus be appreciated that interior portions of the cylinder 22 and piston 24 form a portion of the passageway(s) 82 in the nested arrangement. As noted above, and shown in FIG. 3, junction member 64 and conductor plug 66 of gas control signal wire 54 are interconnected with a gas supply means 88 for use of apparatus 10. Such gas supply means may be a "BEAMER ONE" electrosurgical cart by Beacon Laboratories, Inc. of Denver, Col., U.S.A., or any other arrangement comprising an inert gas reservoir (e.g. tank) and an interconnected control means therefor (e.g. electronically actuated control valve), as will be appreciated by those skilled in the art.

Standard plug 63 of RF signal supply wire 42 is interconnected with a standard electrosurgical generator 86 for use with apparatus 10. By way of example only, electrosurgical generator 86 may be any of the following or equivalents thereof: the "FORCE 2" or "FORCE 4" generators of Vallylab, Inc,; the "EMS 3000," "EMS 4400," or "EMS 5000" of Bard Electro Medical Systems, Inc., the "ACC 450," "ACC 470" or "MCC 350" of Erbe Electro Medical Equipment; the "X10" of Bovi, Inc.; the "9000" by Concept, Inc.; or the "EXCALIBER," "MH 380" or "MH 450" of Aspen Laboratories, Inc. These products are designed to receive standard plug 63, and can be preset to selectively provide an appropriate first predetermined RF signal (e.g. 1 to 300 watts) for tissue cutting and an appropriate second predetermined RF signal (e.g. 1 to 120 watts) for coagulation.

The apparatus 10 can be employed in laparoscopic surgery as follows. First, the surgeon makes a small incision to allow insertion of the access cannula. The access cannula, which may be provided at its leading edge with a trocar, is then inserted into the patient to provide access to the surgical area. Thereafter, the electrode 12 and nozzle 14 are inserted through the access cannula, as will be described below, to the surgical site. The surgeon positions the electrode 12 and nozzle 14 for surgery with the aid of an optical system which provides a view of the surgical site. The electrode 12 can be moved from the nested position to the exposed position by gripping the nose portion 18 and pushing the tail portion 24 so that the electrode 12 is slidably extended relative to the nozzle 14. In this regard, it is noted that a close fit may be provided between the access cannula and the cannula 68 such that the cannula 68 tends to remain stationary relative to the access cannula due to frictional forces as the electrode slides therethrough. Of course, the electrode 12 and nozzle 14 are positioned beyond the end of the access cannula for surgery. It is an advantage of the present invention that the electrode 12 and nozzle 14 can be positioned for surgery in a nested arrangement thereby guarding against tissue puncturing and electrode/tissue or body fluid contact.

To initiate conventional, first mode tissue cutting, apparatus 10 is arranged in the arrangement of FIG. 2 and first bulge portion 48 is pressed by the user to initiate the provision of the preset cut signal from electrosurgical generator 86, through RF signal supply wire 42 and circuit board 34 to electrode 12. The release of pressure from first bulge portion 48 will, of course, terminate the cut signal. When conventional first mode coagulation procedures are to be initiated, second bulge portion 52 is pressed by the user to initiate the provision of the preset RF coagulation signal from electrosurgical generator 86, through RF signal supply wire 42 and circuit board 34 to electrode 12. To initiate second mode gas-enhanced fulguration, apparatus 10 is arranged in the arrangement of FIG. 1 and the user simply presses second bulge portion 52 harder, thereby closing switch 50 such that gas supply signal wire 54 provides a signal to the gas supply means 88 to initiate the supply of inert gas through supply hose 56 and passageway(s) 82 of the apparatus 10, to the nozzle 12.

Figure 7:
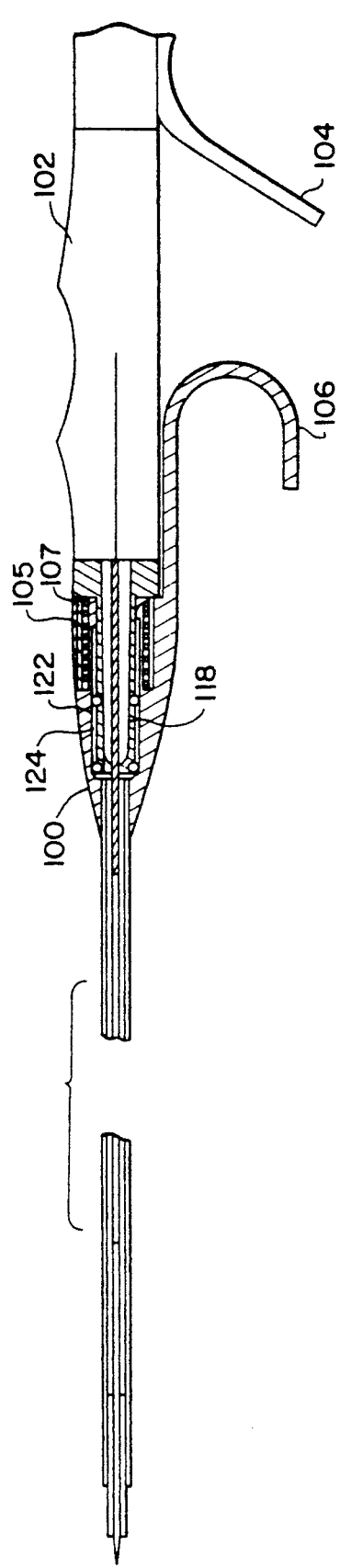
FIG. 7 is a side elevational view of the embodiment of FIG. 4 wherein the electrode and nozzle are positioned so that the electrode is exposed.

Referring to FIGS. 4-7, perspective views (FIGS. 4 and 5) and side elevational views (FIGS. 6 and 7) of an apparatus 90 constructed in accordance with an alternative embodiment of the present invention are shown. The apparatus 90 comprises a surgical assembly including a conventional electrode 92 and a gas delivery nozzle 94, a cannula 96, and a pencil housing 98 including a nose portion 100 and slidably interconnected tail portion 102. FIGS. 4-7 show the apparatus 90 wherein electrode 92 is in a nested position relative to nozzle 94 for gas-enhanced, second-mode operation (FIGS. 4 and 6), and wherein electrode 92 is exposed for conventional first-mode operation (FIGS. 5 and 7).

The tail portion 102 is provided with an integral or interconnected tail portion handle 104, and the nose portion 100 is provided with an integral or interconnected nose portion handle 106, to facilitate movement of the tail portion 102 and electrode 92 relative to the nose portion 100 and nozzle 94. Preferably, handles 104 and 106 are shaped and positioned for ease of handling during surgery. As illustrated, the handles 104 and 106 are constructed in a generally pistol-like arrangement to allow single-hand control.

Figure 4:
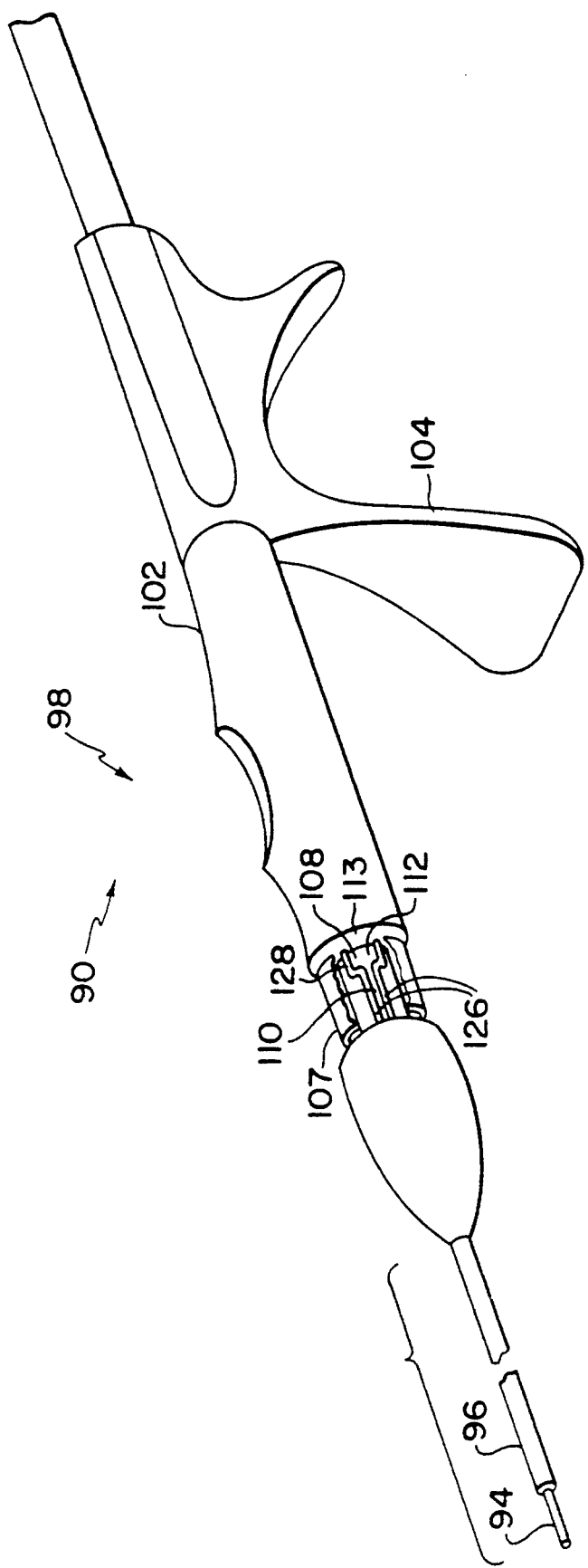
FIG. 4 is a perspective view of an alternate embodiment of the present invention with the electrode and nozzle positioned in a nested arrangement.
Figure 6:
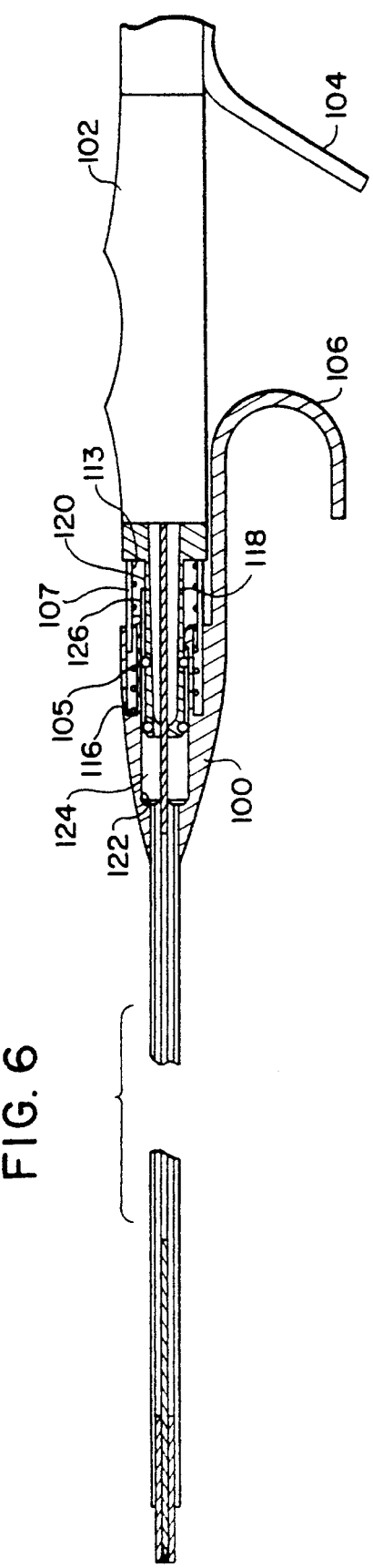
FIG. 6 is a side elevational view of the embodiment of FIG. 4 with the electrode and nozzle positioned in a nested arrangement.

The apparatus 90 further comprises a spring 105 or other resilient member operatively disposed between the nose portion 100 and tail portion 102 to urge the portions 102 and 104 apart so that electrode 92 maintains the nested position of FIGS. 4 and 6. As shown, spring 105 bears against a shoulder 113 of tail portion 102 and against a base 116 of recess 111 in nose portion 100. When conventional first mode operation is desired, an operator can use the handles 104 and 106 to move the apparatus 90 to the arrangement of FIGS. 5 and 7.

A locking assembly may be provided to maintain the apparatus 90 in the first mode arrangement. For example, mating members may be provided on opposing surfaces of the nose portion 100 and tail portion 102 to secure the apparatus 90 in the first mode arrangement. In the illustrated embodiment, the locking assembly comprises a slot 108 formed on the external surface 118 of tail piston 120 and a protrusion 109 extending inwardly into slot 108 from an inside surface 122 of nose cylinder 124. The slot 108 includes a longitudinal portion 110 and a transverse portion 112. The longitudinal portion 110 is defined by a pair of generally parallel longitudinal ridges 126 and the transverse portion 112 is defined by ridges 128 and shoulder 113.

The locking assembly further includes a sleeve 107 to guard against entry of dust or dirt and contain spring 105. Thus, the sleeve 107 is slidably received within recess 111, and the protrusion 109 slides within slot 108, as the apparatus is moved from the nested arrangement of FIGS. 4 and 6 to the exposed position of FIGS. 5-7. The apparatus 90 is locked in the exposed, first mode arrangement by rotating nose portion 100 as shown in FIG. 5 so that the protrusion is received within transverse portion 112. Of course, slot 108 could be formed on the internal surface 122 of cylinder 124, the protrusion 109 could extend from the external surface 118 of cylinder 124, and the orientation of the slot 108 could be reversed to achieve the same result. Additionally, a second transverse portion (not shown) of slot 108 could be provided at the opposite end of slot 108 from transverse portion 112 to lock the apparatus 90 in the nested arrangement, thereby further protecting against undesired electrode 12 exposure.

It is an advantage of the present invention that an electrosurgical apparatus is provided wherein the electrode and nozzle can be maintained in a nested arrangement when the apparatus is inactive, such as when the electrode is being positioned for surgery or when the apparatus is not in use. It is a further advantage of the present invention that such an apparatus is capable of functioning in a conventional electrosurgery mode as well as in a gas-enhanced electrosurgery mode. Another advantage of the present invention is that a dual mode electrosurgical apparatus is provided which is adapted for laparoscopic applications. Also, the present invention allows an operator to maintain simple manual control of the relative positioning of the electrode and nozzle during surgery. Other advantages will be apparent to those skilled in the art.

While the present invention has been described in relation to specific embodiments comprising numerous beneficial features, numerous alternative embodiments are believed to fall within the broad scope of the invention. For example, and without limitation, while the preferred embodiment conveniently provides first and second mode control switches directly on the gripping portion of a pencil housing, such switches could be separately provided. For example, the gas supply switch 50 of the embodiment of FIGS. 1-3 could be separately provided at a third bulge location (not shown) on the apparatus 10 and/or totally separate via a foot switch 114 connected to the gas supply means 88, as shown in FIG. 3. Similarly, a 2-wire switch for selectively initiating tissue cutting and/or coagulation could be separately provided in a foot switch connected to a gas supply means 88. Additionally, although the present invention is advantageously employed in dual mode, laparoscopic applications, numerous features of the invention, including without limitation the ability to maintain the electrode and nozzle in a nested arrangement when the apparatus is inactive,, are considered to be applicable to non-dual mode and/or non-laparoscopic applications.

Additional alternative embodiments apparent to those skilled in the art in view of the foregoing are intended to be within the scope of the present invention as further defined by the claims set forth below.

What is claimed is:

1. An electrosurgical instrument comprising:
    a surgical assembly including a nozzle and an electrode having a common longitudinal axis, the nozzle positioned about at least a portion of the electrode;
    first means for arranging said assembly between a first arrangement wherein said electrode is exposed and a second arrangement wherein said electrode and said nozzle are substantially nested;
    second means for maintaining said assembly in said second arrangement when said assembly is in an inactive state; and
    third means for forward delivering a gas to said nozzle when said assembly is in said first arrangement.

2. The instrument of claim 1, further comprising mode selection means, operatively associated with said surgical assembly, for selecting between a first operative mode and a second operative mode.

3. The instrument of claim 2, wherein said mode selection means comprises a pressure switch to control delivery of gas to said nozzle.

4. The instrument of claim 2, further comprising means for holding said assembly in said first arrangement during said first operative mode.

5. The instrument of claim 4, wherein said means for holding comprises a first mating member integral with one of said electrode and said nozzle and a second mating member integral with the other of said electrode and said nozzle wherein said first member is matingly engaged by said second member when said assembly is in said first arrangement.

6. The instrument of claim 4, wherein said means for holding comprises a protrusion integrally connected to one of said electrode and said nozzle, and a slot integrally connected to the other of said electrode and said nozzle to slidably receive said protrusion, the slot having a longitudinal portion and a transverse portion, wherein said assembly is held in said first arrangement when said protrusion is received within said transverse portion of said slot.

7. The instrument of claim 1, wherein said f first means comprises a housing including a first portion integrally connected to said nozzle and a second portion integrally connected to said electrode, said first portion being slidably interconnected to said second portion.

8. The instrument in claim 7, wherein said second means comprises a resilient member operatively disposed between said first portion and said second portion to maintain said assembly in said second arrangement.

9. The instrument of claim 7, wherein said second means comprises a first mating member integral with said first portion and a second mating member integral with said second portion, wherein said first member is matingly engaged by said second member when said assembly is in said second arrangement.

10. The instrument of claim 7, further comprising an elongated tube between said housing and said nozzle to allow laparoscopic application of paid assembly.

11. The instrument of claim 10, wherein said nozzle is fixedly interconnected to said tube.

12. The instrument of claim 7, wherein said first means comprises a laterally extending member integral with said first portion wherein said assembly is arranged by gripping said member.

13. The instrument of claim 12, wherein said first means further comprises a second laterally extending member integral with said second portion wherein said assembly is arrangeable by gripping said first member and said second member with a single hand.

14. The instrument of claim 1, further comprising signal control means for selectively controlling the supply of an electrical signal to the electrode from a power source.

15. The instrument of claim 14, wherein said signal control means comprises switching means for selectively switching said signal between at least a first signal sufficient for tissue cutting and a second signal sufficient for coagulation.

16. An electrosurgical instrument comprising:
    a nozzle and an electrode having a common longitudinal axis, the nozzle positioned about at least a portion of the electrode;
    means for moving said electrode relative to said nozzle between a first position for a first operative mode and a second position for a second operative mode wherein the electrode is in a more forward position relative to the nozzle in said first position than in said second position;
    means for maintaining said electrode in said second position during said second operative mode; and
    means for forward delivery of gas to said nozzle during said first operative mode.

17. The instrument of claim 16, wherein said means for maintaining comprises a resilient member disposed between a first portion of said instrument connected to said nozzle and a second portion of said instrument connected to said electrode to urge said first portion and said second portion apart.

18. An electrosurgical apparatus, comprising:
    a cannula;
    an electrode and a nozzle having a common longitudinal axis, the nozzle positioned about at least a portion of the electrode and fixedly attached to said cannula;
    positioning means for moving said electrode relative to said nozzle between a first position for non-gas-enhanced electrosurgery and a second position for gas-enhanced electrosurgery, wherein the electrode is more forward relative to the nozzle in the first position than in the second position; and
    gas delivery means for forward delivery of gas to said nozzle for gas-enhanced electrosurgery.

19. The apparatus of claim 18 further comprising:
    holding means for holding said electrode in said first position.

20. The apparatus of claim 18, further comprising means for maintaining said electrode in said second position.

21. An electrosurgical instrument, comprising:
    an electrode and a nozzle having a common longitudinal axis, the nozzle positioned about at least a portion of the electrode;

a pencil housing having a first portion and a second portion, the first and second portions being slidably interconnected for relative movement therebetween, wherein one of the first portion and the second portion is interconnected to said electrode and the other of the first portion and the second portion is interconnected to said nozzle; and means for forward delivering a gas to said nozzle.

22. The apparatus of claim 21, wherein said electrode is moveable from a first position wherein the electrode extends forwardly beyond an end of said nozzle and a second position wherein said electrode and said nozzle are substantially nested by sliding said first portion relative to said second portion.

23. An electrosurgical pencil, comprising:

an elongated housing, an electrode and a nozzle having a common longitudinal axis and being interconnected to said housing for relative axial movement between said electrode and nozzle along said axis, said nozzle being located about at least a portion of said electrode, positioning means interconnected to said housing and operatively associated with at least one of said nozzle and said electrode for axially positioning said electrode and said nozzle relative to each other in a first relative position for a first, non-gas enhanced mode of operation and a second relative position for a second, gas enhanced mode of operation, wherein the nozzle is more forward relative to the electrode in said second relative position than in said first relative position; and gas delivery means for forward delivery of a gas past said electrode during said second mode of operation for gas enhanced electrosurgery.

24. The electrosurgical pencil as recited in claim 23, wherein said nozzle is stationary and said electrode is movable relative thereto.

* * * * *